United States Patent [19]

Chanoch

[11] Patent Number: 5,582,598

[45] Date of Patent: Dec. 10, 1996

[54] MEDICATION DELIVERY PEN WITH VARIABLE INCREMENT DOSE SCALE

[75] Inventor: Lawrence H. Chanoch, Mahwah, N.J.

[73] Assignee: Becton Dickinson and Company, Franklin Lakes, N.J.

[21] Appl. No.: 308,767

[22] Filed: Sep. 19, 1994

[51] Int. Cl.[6] .................................................. A61M 5/00
[52] U.S. Cl. ........................... 604/208; 604/211; 604/232; 604/218; 222/309
[58] Field of Search ..................... 604/132, 131, 604/207–211, 232, 234, 187, 186, 71, 72, 224, 218; 222/46, 48, 309

[56] References Cited

U.S. PATENT DOCUMENTS

| | | | |
|---|---|---|---|
| 5,112,317 | 5/1992 | Michel | 604/232 |
| 5,114,406 | 5/1992 | Gabriel et al. | 604/232 |
| 5,279,585 | 1/1994 | Balkwill | 604/211 |
| 5,304,152 | 4/1994 | Sams | 604/211 |

Primary Examiner—John D. Yasko
Assistant Examiner—Ronald K. Stright, Jr.
Attorney, Agent, or Firm—Alan W. Fiedler

[57] ABSTRACT

A medication delivery pen is provided having a pen body assembly and a cartridge assembly that are threadedly engageable with one another. The pen body assembly includes a rotatable driver for driving a cartridge plunger preselected distances that are in accordance with a desired dose of medication to be delivered. The driver providing different preset rates of injection.

8 Claims, 5 Drawing Sheets

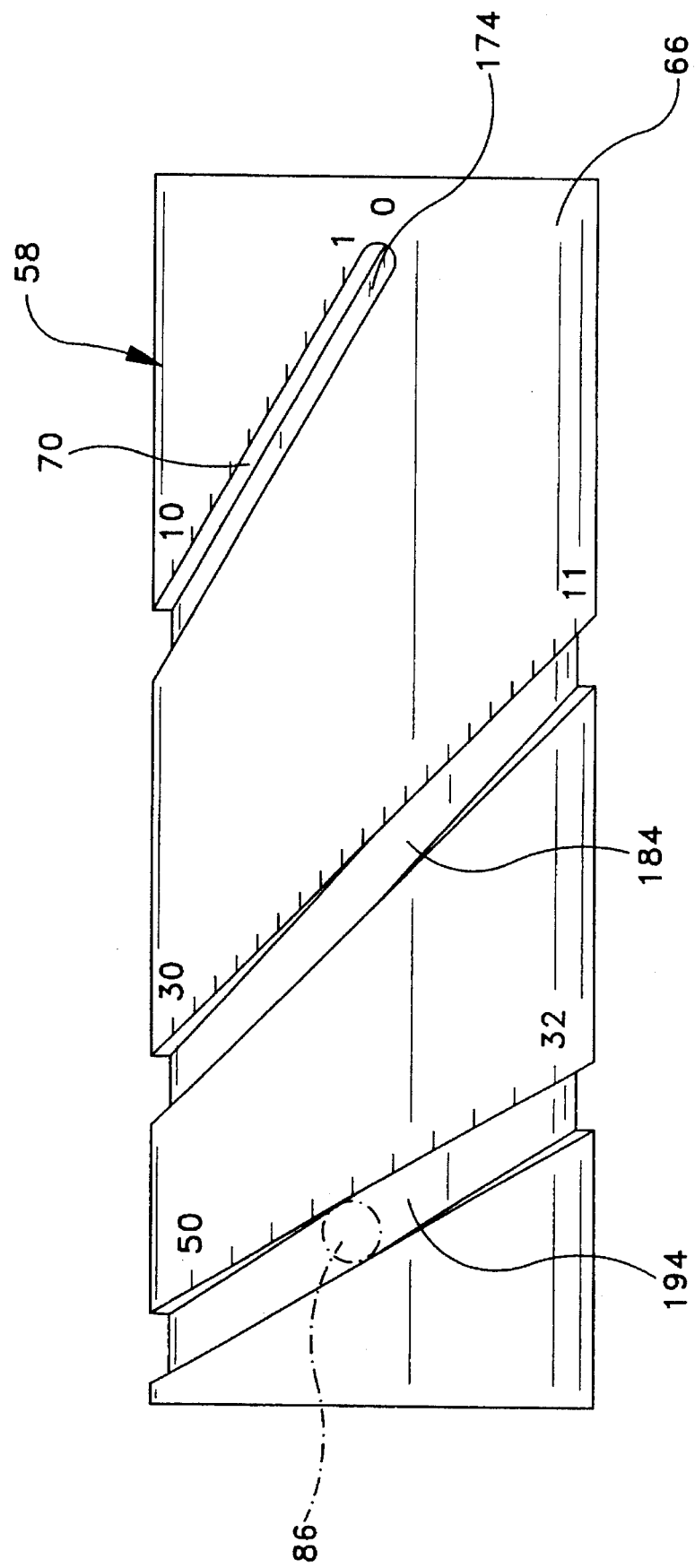

MEDICATION DELIVERY PEN WITH VARIABLE INCREMENT DOSE SCALE

BACKGROUND OF THE INVENTION

1. Field of the Invention

The subject invention relates to medication delivery pens having a cartridge holder assembly and a pen body assembly removably mounted to the cartridge holder assembly for delivering medication having an improved dose setting device.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication is drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described medication delivery pen is effective and much more convenient for self-administration of medication than the typical hypodermic syringe and separate medication vial. However, prior art medication delivery pens are limited to a particular range of dosage amounts because of the fairly complex dosage selecting and driving mechanisms within the delivery pens. To vary the dosage amounts available to a user would require more complex devices that are costly to manufacture. Hence, it is necessary to provide a medication delivery pen at a reasonable cost having a wider range of doses and more flexibility when setting doses for drug delivery.

SUMMARY OF THE INVENTION

The subject invention relates to a medication delivery pen having a medication cartridge assembly that is selectively engageable with and disengageable from a pen body assembly. The medication cartridge assembly is an elongate generally cylindrical structure having opposed proximal and distal ends. The distal end of the medication cartridge assembly includes needle mounting means for securely but releasably receiving a needle cannula assembly, the distal end being characterized by a pierceable elastomeric seal that may be repeatedly and resealable pierced by the proximal end of a double-ended needle cannula. The proximal end of the medication cartridge assembly includes body mounting means for securely but releasably mounting the medication cartridge assembly to the pen body assembly. The body mounting means may comprise an array of threads extending distally from the proximal end of the medication cartridge assembly.

The medication cartridge assembly further includes plunger means slidably disposed in fluid tight engagement therein. The plunger means may initially be disposed in a proximal position within the medication cartridge assembly and may be moved in a distal direction by a driver projecting from the pen body assembly. The medication cartridge assembly further comprises anti-rotation means for preventing rotation of the driver.

The pen body assembly of the subject invention comprises an array of mounting threads to enable threaded engagement of the pen body assembly and the medication cartridge assembly and an actuator button rotatably mounted on its proximal end. Thus, axial forces exerted on the actuator button cause the pen body assembly to threadedly engage the medication cartridge assembly.

The pen body assembly further includes a lead screw for selectively engaging the plunger of the cartridge assembly and for urging the plunger of the cartridge assembly in a distal direction. At least a portion of the lead screw includes driving threads engaged with other portions of the pen body assembly that may be operative to achieve axial movement of the lead screw in response to axial forces exerted on the rotatable actuator button. The pen body assembly further comprises dose setting means for establishing and precisely controlling the amount of medication to be delivered in response to each actuation of the actuator button. The dose setting means may be any of several structures as described in greater detail below.

A cartridge assembly that is filed with medication is mounted to the pen body assembly and the initial response to forces on the actuator button cause the lead screw to move in a proximal direction toward its starting position, while the remaining portions of the pen body assembly move distally toward the vial assembly. Further forces exerted on the actuator button cause the mounting means of the pen body to engage the mounting means of the cartridge assembly. Continued axial forces on the actuator button cause the mounting threads to engage the cartridge assembly and continue the proximal movement of the driver. The pen body assembly is fully but releasably engaged with the cartridge assembly at the same time that the driver is at its proximal extreme position and is then in position to begin delivering selected doses of medication from the pen. Doses of medication can be dispensed as needed over time, and the cartridge assembly is removed and discarded when the medication therein has been exhausted. A new medication cartridge assembly may then be mounted to the pen body assembly as described above.

The driving means in the pen body assembly of the present invention includes a dose setting knob having a helical groove with three different regions of operation, each region having a different pitch to provide three different types of dosage increments. For example, the dose setting increments in the first region are 0.5 within a dose range of 0 to 10 units, 1.0 in the 10 to 30 unit range of the second region, and 2.0 for doses above 30 units in the third region. This approach to dose setting and the associated resolution (ability to select a particular dose) is believed to be more consistent with the way insulin doses are prescribed by physicians and the way patients are instructed to adjust their own insulin dose,

DESCRIPTION OF THE DRAWINGS

FIG. 5 is a side view of the periphery of a dose knob of the present invention operating in a third region and projected on a plane.

DETAILED DESCRIPTION

Figure 1:
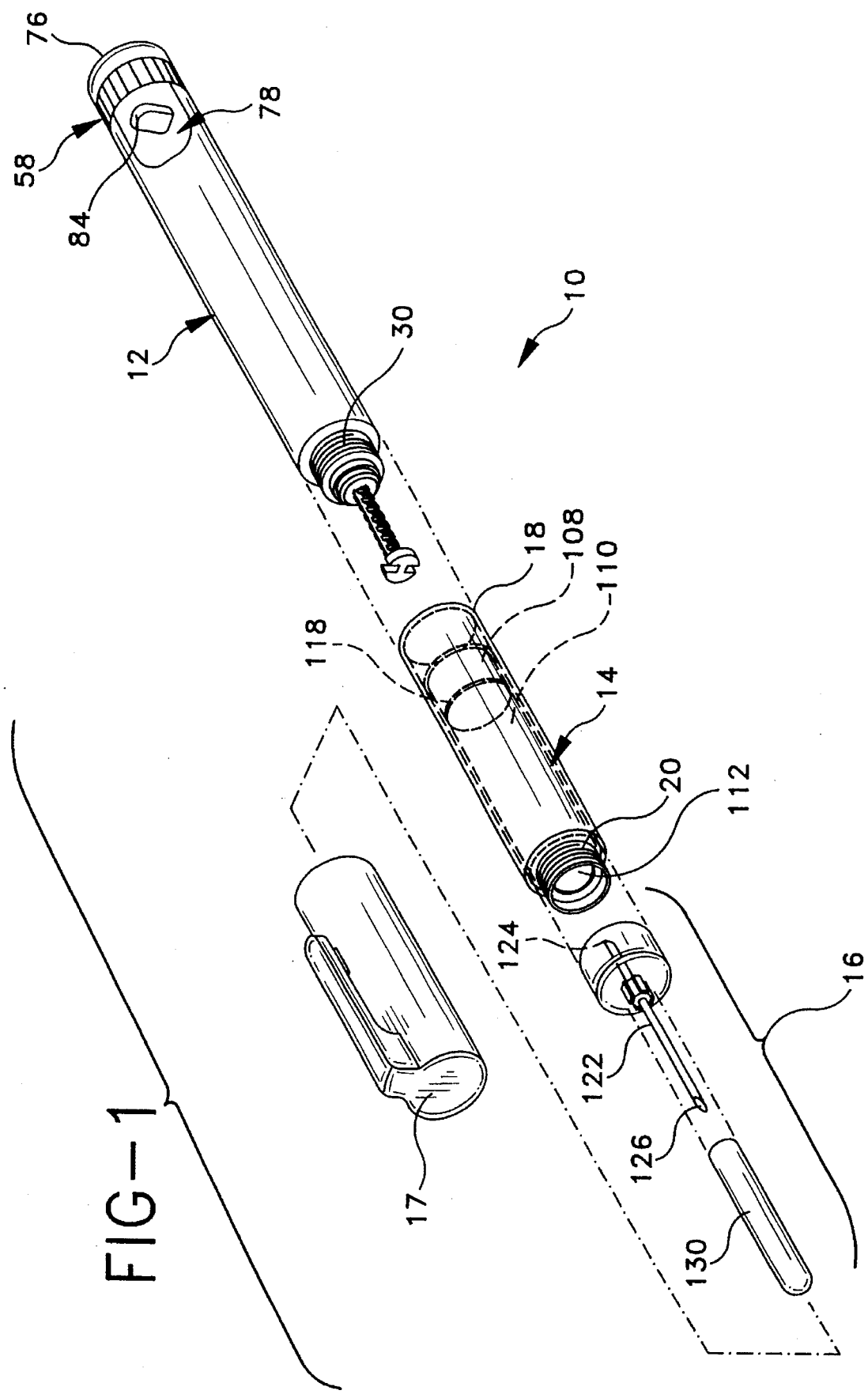
FIG. 1 is a perspective view of the medication delivery pen of the subject invention.

A medication delivery pen in accordance with the subject invention is identified generally by the numeral 10 in FIG. 1. Medication delivery pen 10 includes a pen body assembly 12, a cartridge assembly 14, a needle cannula assembly 16 and a cap 17. Cartridge assembly 14 includes opposed proximal and distal ends 18 and 20, respectively. Proximal end 18 of cartridge assembly 14 is dimensioned and configured to threadedly engage pen body assembly 12, as explained further herein. Distal end 20 of cartridge assembly 14 is configured to securely but releasably engage needle cannula assembly 16 and a shield 130 is provided to cover a distal end 126 of a needle cannula 122 in needle cannula assembly 16.

Figure 2:
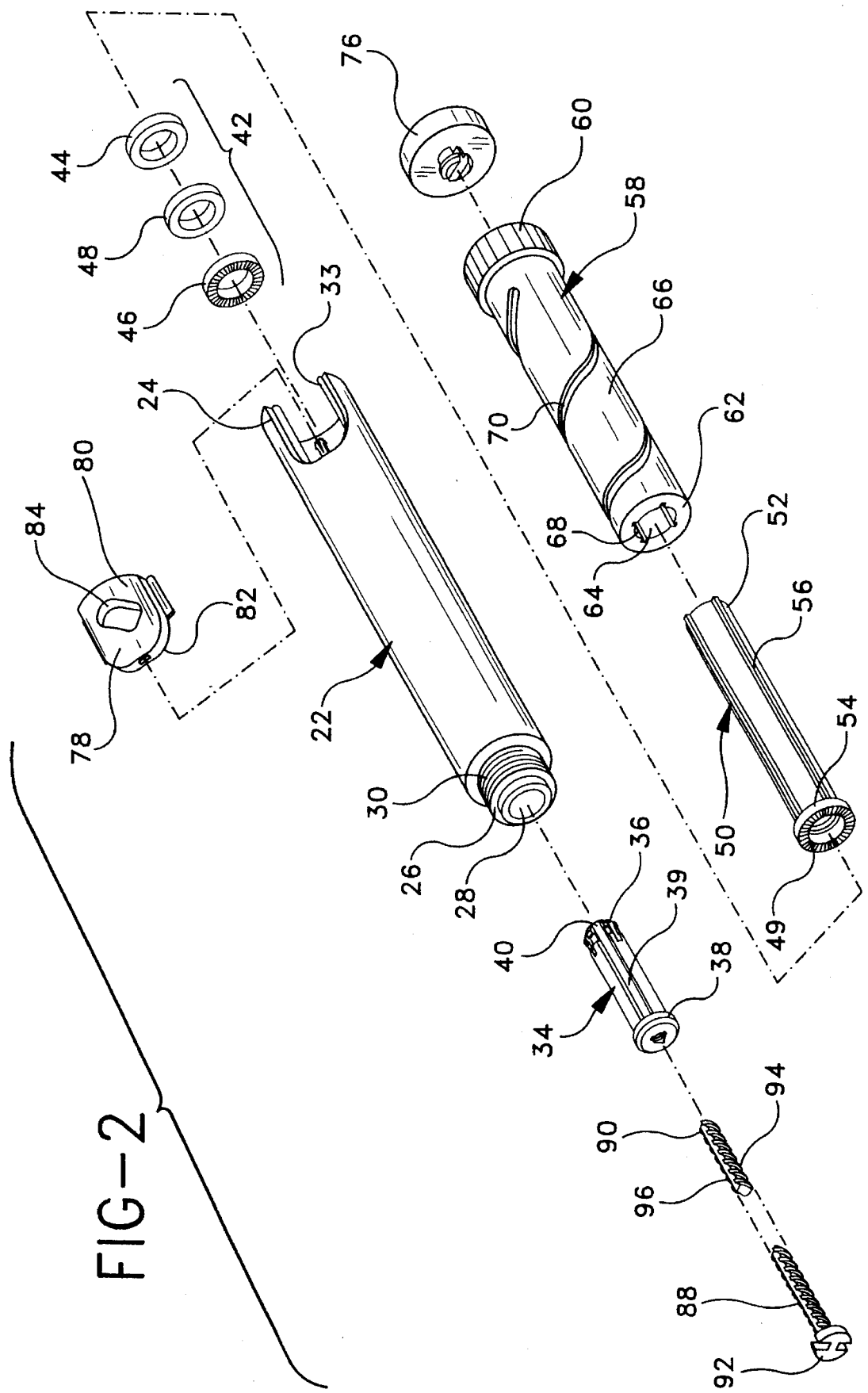
FIG. 2 is an exploded perspective view of the pen body assembly of the medication delivery pen shown in FIG. 1.

The preferred embodiment of pen body assembly 12 is illustrated in greater detail in FIG. 2. It is understood, however, that variations from this preferred embodiment is provided, and are considered to be within the scope of the subject invention. Pen body assembly 12 includes a generally cylindrical housing 22 having opposed proximal and distal ends 24 and 26, and a substantially hollow throughbore 28 extending axially therethrough. An array of external threads 30 extends proximally from distal end 26 for threaded engagement with proximal end 18 of cartridge holder assembly 14. Portions of hollow throughbore 28 of housing 22 adjacent distal end 26 are characterized by an array of clutch teeth (not shown) molded therein. Proximal end 24 of housing 22 is characterized by a cut-out 33 formed therein for receiving a window insert 78.

Pen body assembly 12 includes a nut 34 having opposed proximal and distal ends 36 and 38, respectively. Exterior surface regions of nut 34 between proximal and distal ends 36 and 38 define a plurality of longitudinally extending splines 39. Proximal end 36 of nut 34 also includes a plurality of longitudinally extending resilient fingers 40 with enlarged ends that enable snap engagement of nut 34 into other portions of pen body assembly 12, as explained further herein. Distal end 38 of nut 34 is radially enlarged to limit axial movement of nut 34 in distal end 26 of housing 22. Thus, nut 34 is axially constrained within housing 22, however, the dimensions and configurations of nut 34 and housing 22 permit free relative rotation therebetween.

Pen body assembly 12 includes a clutch assembly 42 mounted therein. Clutch assembly 42 includes a proximal clutch 44, a distal clutch 46 and an annular spring 48 biasingly engaged therebetween. Proximal and distal clutches 44 and 46 each are configured for non-rotatable engagement over splines 39 of nut 34. Distal clutch 46 includes an army of distally facing saw teeth dimensioned, disposed and configured for engagement with clutch teeth (not shown) on the interior distal end of housing 22, such that distal clutch 46 can rotate only in one direction relative to housing 22. Proximal clutch 44 includes an army of proximally facing teeth which are also configured for unidirectional rotation, as explained further herein.

Pen body assembly 12 includes a generally cylindrical driver 50 having opposed proximal and distal ends 52 and 54. Driver 50 is slidably inserted into housing 22 of pen body assembly 12 such that distal end 54 of driver 50 is snap fit over the enlarged ends of resilient fingers 40 at proximal end 36 of nut 34. This snap fit engagement prevents axial movement between nut 34 and driver 50, but permits free relative rotational movement within housing 22. Distal end 54 of driver 50 is also characterized by an army of saw teeth 49 that engage with the saw teeth on proximal clutch 44. Outer surface regions of driver 50 are characterized by splines 56 extending radially outwardly thereon and along a substantial portion of the length of driver 50.

Pen body assembly 12 includes a dose knob 58 which is a hollow generally cylindrical structure having opposed proximal and distal ends 60 and 62 and opposed inner and outer surfaces 64 and 66. Inner surface 64 is characterized by longitudinally extending grooves 68 which are disposed and dimensioned for engagement with splines 56 on driver 50. More particularly, dose knob 58 is spline mounted over driver 50 within housing 22 of pen body assembly 12. Thus, axially extending grooves 68 in dose knob 58 engage splines 56 of driver 50 to prevent relative rotation therebetween, but permitting relative axial movement.

Figure 3:
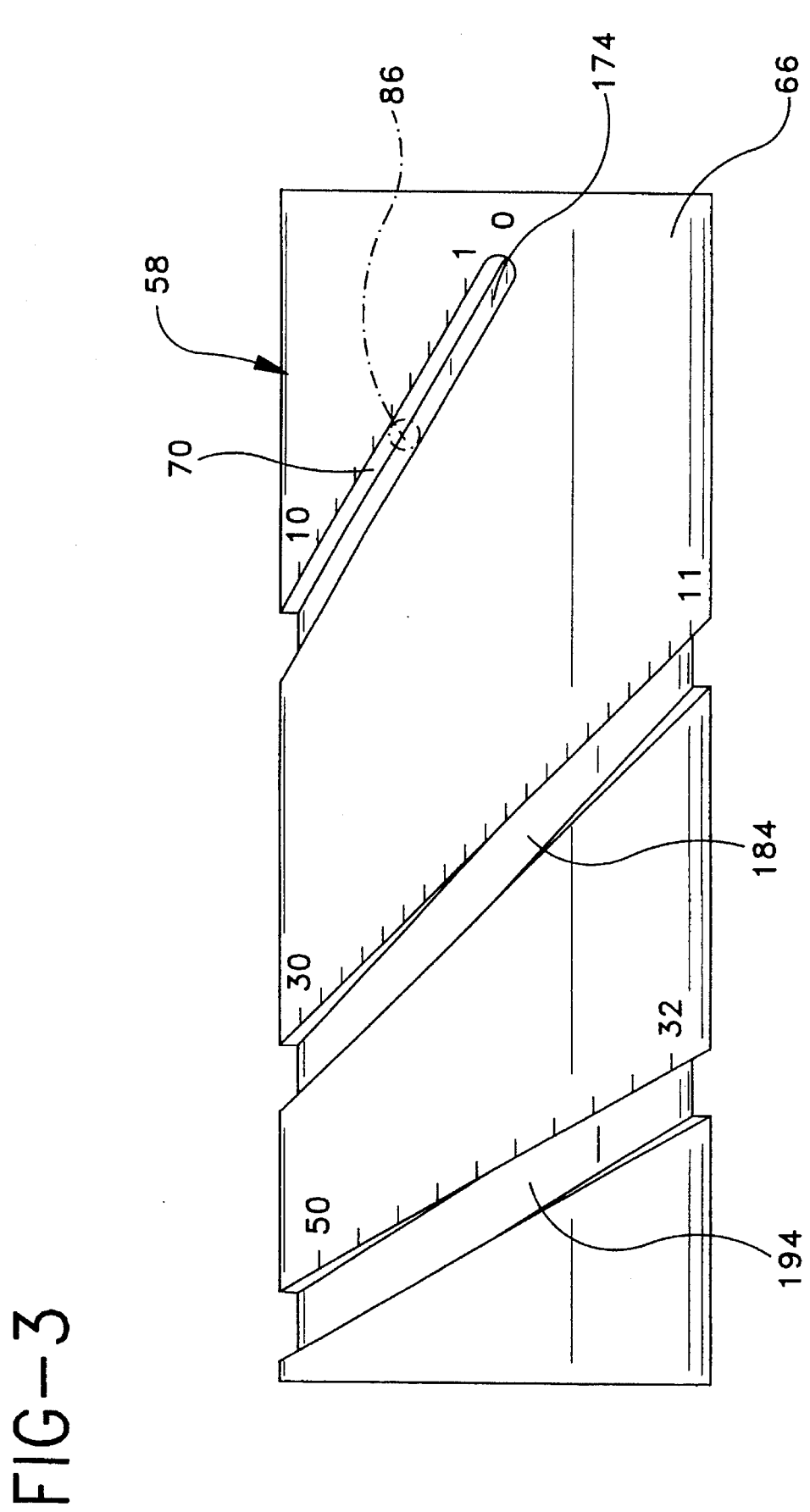
FIG. 3 is a side view of the periphery of a dose knob of the present invention operating in a first region and projected on a plane.
Figure 4:
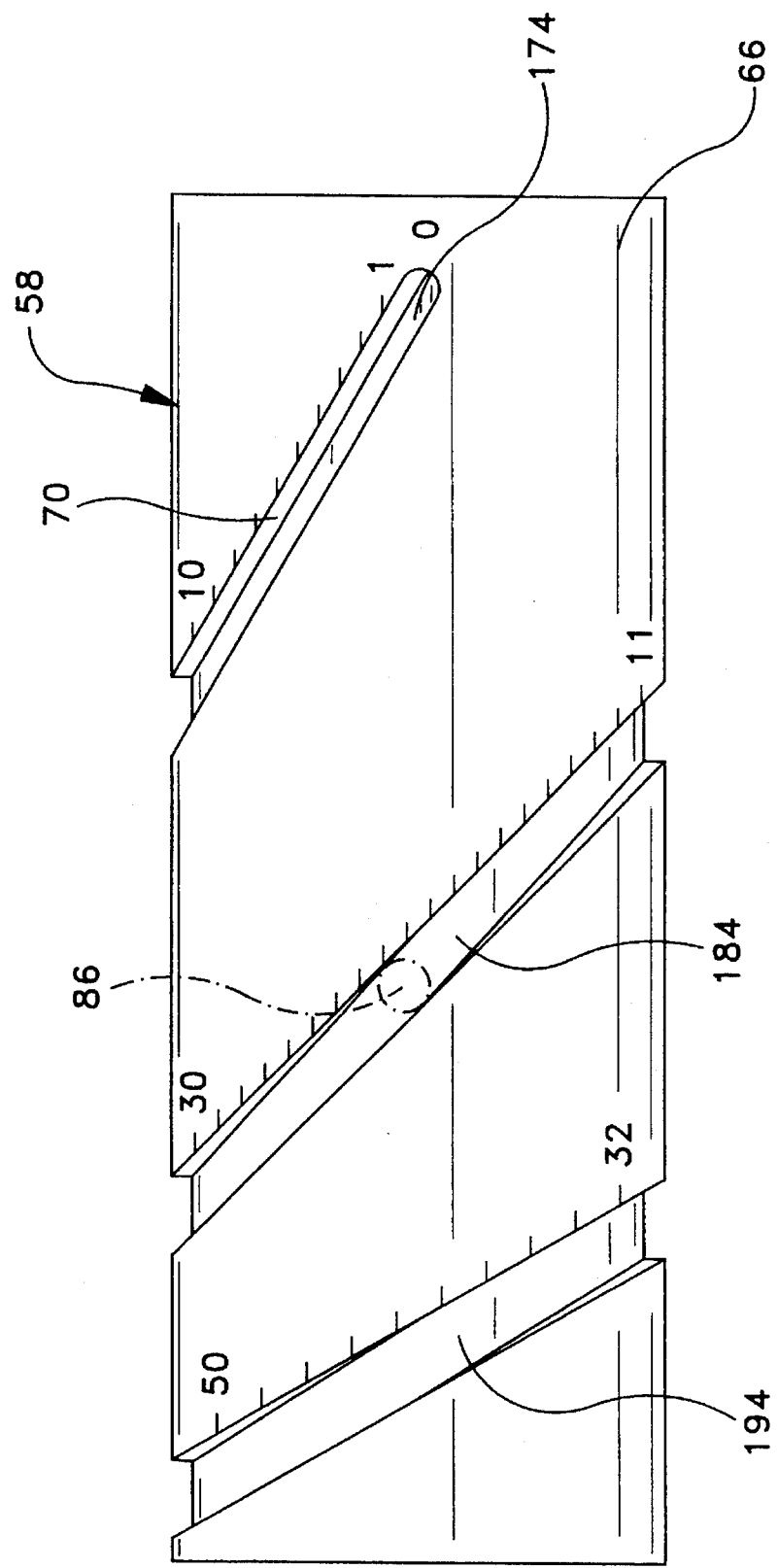
FIG. 4 is a side view of the periphery of a dose knob of the present invention operating in a second region and projected on a plane.

FIGS. 3–5 are side views of the periphery of dose setting knob 58 projected on a plane and show button 86 operating in a first, second and third region, respectively. As shown in FIGS. 3–5, outer surface 66 of dose knob 58 is characterized by a groove 70 comprised of three regions, each region having a helical component 174, 184, 194. Each helical component has a different pitch to provide different dose increments in each region of dose setting knob 58 and thereby improve resolution and provide a greater range of potential dosage settings for the pen. Outer surface 66 adjacent each helical component 174, 184, 194 of groove 70 is provided with dosage indicia to define dose setting increments corresponding to each region of groove 70. For example, the dose setting increments are 0.5 in the dose range 0 to 10 units of helical component 174, 1.0 in the 10 to 30 unit range of helical component 184, and 2.0 for doses above 30 units in helical component 194. The present invention provides dosage resolution very consistent with the way insulin doses are prescribed by physicians, and the way patients are instructed to adjust their own insulin dosages.

Proximal end 60 of dose knob 58 is characterized by a gnarled exterior surface to facilitate manipulation for setting a selected dose. An actuator button 76 is snapped into engagement with proximal end 60 of dose knob 58 to permit relative rotation therebetween. An insert 78 is snapped into engagement with cut-out 33 in proximal end 24 of housing 22, insert 78 including opposed inner and outer surfaces 82 and 80 and a window 84 extending therebetween. Inner surface 82 of insert 78 includes a projection 86, shown in FIGS. 3–5, on inner surface 82 dimensioned and disposed to engage in groove 70 of dose knob 58. Projection 86 and window 84 are also disposed to enable the indicia on dose knob 58 to be visible through window 84.

Pen body assembly 12 further includes a lead screw 88 with opposed proximal and distal ends 90 and 92 and an array of external threads 94. External threads 94 are characterized, however, by a pair of opposed axially extending grooves 96 which extend from distal end 92 substantially to the proximal end 90. Threads 94 are engaged in nut 34, such that proximal end 90 of lead screw 88 is within housing 22 and distal end 92 projects distally beyond housing 22. Threads 94 on lead screw 88 have exactly the same pitch and the same hand as threads 30 on distal end 26 of housing 22.

Pen body assembly 12 is assembled by placing nut 34 into housing 22 from distal end 26. Clutch assembly 42 then is mounted over splines 39 on nut 34. Driver 50 is then inserted into proximal end 24 of housing 22, and is urged sufficiently in a distal direction for snap fit engagement with nut 34. In this snapped engagement, the saw teeth of distal clutch 46 will be secured in engagement with the teeth in housing 22, and the saw teeth of proximal clutch 44 will be engaged with saw teeth 49 at distal end 54 of driver 50. Spring 48 will maintain constant selected pressure between these interengaged saw teeth. Insert 78 then is positioned over dose knob 58 such that projection 86 of insert 78 is engaged in groove 70 in dose knob 58. The temporarily assembled insert 78 and dose knob 58 then are urged into housing 22. Lead screw 88 then is threaded into nut 34, and actuator button 76 is snapped into engagement with proximal end 60 of dose knob 58.

The assembled pen body assembly 12 and cartridge assembly 14, shown in FIG. 1, is stored until a selected dose of medication is required. Just prior to use, needle cannula assembly 16 is threadedly engaged to distal end 20 of cartridge assembly 14. This threaded engagement will cause a proximal tip 124 of needle cannula 122 to pierce a pierceable elestomeric seal 112 on the medication cartridge and provide commmunication with medication therein. Shield 130 may then be removed. A desired dose of medication is set by rotating dose knob 58 until indicia corresponding to the desired dose appears in window 84 of insert 78. The engagement of projection 86 on insert 78 in helical portions 174, 184, 194 of groove 70 in dose knob 58 causes a threaded retraction of dose knob 58 relative to housing 22 of pen body assembly 12. This threaded retraction of dose knob 58 will cause a simultaneous rotation of driver 50 splined thereto. However, nut 34 will not rotate because the saw teeth on distal clutch 46 and the saw teeth on interior portions of housing 22 are locked to prevent rotation in that direction. Proximal clutch 44 is splined to nut 34, and hence also will not turn. However, saw teeth 49 at distal end 54 of driver 50 are shaped to allow rotation relative to proximal clutch 44, and provide an audible click for each unit of medication in the selected dose. This is helpful for visually impaired patients who may be required to set doses and administer insulin or other medication to themselves. Annular spring 48 contributes to the engagement that provides these audible clicking sounds.

When the desired dose is set, injection is achieved by merely pushing on actuator button 76. This causes dose knob 58 to turn about helixes 174, 184, 194 relative to pen body housing 22, so that driver 50 rotates through the same number of degrees. As dose knob 58 turns about helixes 174, 184, 194, projection 86 travels through helix 174 in the first region when dispensing 1 to 10 units of medication, helix 184 in the second region when dispensing 11 to 30 units of medication, and helix 194 in the third region when dispensing 31 to 50 units of medication. Dose setting knob 58 of the present invention therefore provides a wider range of dosages for the user than previously known dose setting knobs because of the different pitch of each helix, as shown in FIGS. 3–5. Rotation of dose setting knob 58 is opposite to the rotation generated during the dose setting procedure, when the rotational freedom of clutch assembly 42 is reversed. As dose setting knob 58 turns during injection the previously clicking proximal clutch 44 is locked to and turns with driver 50. This driving movement of proximal clutch 44 causes a corresponding rotational movement of nut 34 because of the splined engagement therebetween. Distal clutch 46 is therefore free to rotate against the saw teeth in housing 22, and makes an audible clicking indication during injection of medication.

Rotation of lead screw 88 is prevented by grooves 96 and tabs unitarily molded within cartridge holder assembly 14.

Therefore, as nut 34 rotates under the driving action of proximal clutch 44 and driver 50, lead screw 88 will be advanced axially into cartridge holder assembly 14. This axial advancement of lead screw 88 causes distal end 92 thereof to urge plunger 118 distally into cartridge 108, and hence causes a particular amount of medication 110 to be injected through needle cannula 122 depending upon the dosage set using dose setting knob 58. Injection is terminated when proximal end 60 of dose knob 58 engages against proximal end 24 of pen body housing 22.

Upon completion of the injection, needle cannula assembly 16 may be disengaged from cartridge holder assembly 14 and safely discarded. Cap 17 may be mounted over cartridge holder assembly 14, and pen 10 may be stored or carried in a convenient location until the next dose of medication is required. A subsequent dose of medication will be set in exactly the manner as described above. However, for such a subsequent dose, lead screw 88 will be in a partly advanced position as a starting point. Dose setting and injections can be carried out until all of the medication has been used. Cartridge holder assembly 14 may then be threadedly disengaged from pen body assembly 12, and slidably separated from lead screw 88. The separated cartridge holder assembly may then be discarded and replaced as described above.

While the invention has been described with respect to a preferred embodiment, it is apparent that various changes can be made without departing from the scope of the invention as defined by the appended claims. In particular, the pen body assembly may have other driving and/or clutch mechanisms. Additionally, different means for preventing and/or enabling rotation during the dose setting and injection phases may be provided. Similarly, other means for mounting needle cannula to the cartridge assembly may be provided. These various optional constructions will be apparent to those skilled in the art after having read the subject disclosure.

What is claimed is:

1. A medication delivery pen comprising:

a medication-containing cartridge assembly having a cartridge with a pierceably sealed distal end, an open proximal end having an array of threads, and a plunger in sliding fluid tight engagement within said cartridge at a location distally of said array of threads; and a pen body assembly having:

a housing with opposed proximal and distal ends, said proximal end having a projection therein and said distal end having an array of threads dimensioned and pitched for threaded engagement with said threads at said proximal end of said cartridge assembly;

a lead screw having a proximal end slidably mounted within said housing, a distal end projecting beyond said distal end of said housing for selective engagement with said plunger, and threads extending between said proximal and distal ends of said lead screw; and a rotatable dose setting knob having a groove for receiving said projection and a plurality of dosage indicia for a predefined range of dosage increments, said groove having at least two differently pitched regions, wherein each pitched region provides for a different amount of rotation with respect to a proximal movement of said dose setting knob, which results in different dosage increments in each pitched region of said dose setting knob, whereby said dose setting knob causes said lead screw to move distally in said pen body assembly a distance corresponding to a selected pitched region of said groove and a selected dosage indicia in the selected pitched region when said dose setting knob is pushed in a distal direction.

2. The medication delivery pen of claim 1, wherein said sealed end of said cartridge assembly comprises a pierceable elastomeric seal, and wherein said cartridge assembly further comprises needle mounting means adjacent said distal end of said cartridge assembly, said medication delivery pen further comprising a needle cannula assembly having a hub selectively engageable with the mounting means of said cartridge assembly and a double-ended needle having opposed proximal and distal points, said proximal point of said needle being dimensioned and disposed to pierce said seal upon engagement with said cartridge assembly.

3. The medication delivery pen of claim 2, further comprising a plurality of needle cannula assemblies, each said needle cannula assembly being selectively engageable and disengageable from said cartridge assembly.

4. The medication delivery pen of claim 1, wherein said pen body assembly includes a driver selectively movable in proximal and distal directions in said pen body assembly housing, said driver connecting said dose setting knob to said lead screw.

5. The medication delivery pen of claim 4, wherein said threads on said lead screw define a pitch substantially identical to said pitch of said threads on said distal end of said housing, said lead screw being axially movable in said housing in response to movement of said driver by said dose setting knob for selectively advancing said lead screw distances from said housing corresponding to selected doses of medication, whereby the substantially identical pitches of said threads on said lead screw and on said housing enables said lead screw to move in said housing simultaneously with threaded engagement of said housing with said cartridge holder assembly.

6. The medication delivery pen of claim 1, wherein said pen body assembly further includes an actuator button rotatably mounted on said dose setting knob, such that axial forces exerted on said actuator button generate movement of said lead screw distally in said pen body assembly and into said cartridge.

7. The medication deliverly pen of claim 1, wherein said dose setting knob defines specified distances of travel for said lead screw corresponding to selected doses of medication to be delivered.

8. A medication delivery pen comprising:

a medication-containing cartridge assembly having opposed proximal and distal ends, an elongate medication-containing cartridge mounted in said cartridge assembly, said cartridge having a sealed distal end, a plunger slidably disposed in fluid tight engagement in said cartridge, medication disposed in said cartridge, said proximal end of said cartridge assembly defining an array of threads; and a pen body assembly having:

a pen body housing with opposed proximal and distal ends, said proximal end of said pen body housing having a projection therein and said distal end of said pen body housing having an array of threads defining a pitch for threaded engagement with said threads at said proximal end of any of said cartridge assembly;

a driver selectively movable in proximal and distal directions in said pen body housing;

a rotatable dose setting knob having a groove for receiving said projection and a plurality of dosage indicia for a predefined range of dosage increments, said groove having at least two differently pitched regions, wherein each pitched region provides for a different amount of rotation with respect to a proximal movement of said dose setting knob, which results in different dosage increments in each pitched region of said dose setting knob, whereby said dose setting knob causes said driver to move distally in said pen body assembly a distance corresponding to a selected pitched region of said groove and a selected dosage indicia in the selected pitched region when said dose setting knob is pushed in a distal direction; and a lead screw having opposed proximal and distal ends, said distal end of said lead screw being selectively engageable with the plunger of any of said cartridge assemblies, said lead screw further comprising an array of external threads thereon threadedly engaged for rotation in said pen body housing, said threads on said lead screw defining a pitch substantially identical to said pitch of said threads on said distal end of said pen body housing, said lead screw being axially movable in said pen body housing in response to movement of said driver for selectively advancing said lead screw distances from said pen body housing corresponding to selected doses of medication, whereby the substantially identical pitches of said threads on said lead screw and on said pen body housing enables said lead screw to move in said pen body housing simultaneously with threaded engagement of said pen body housing with said cartridge assembly.

* * * * *